US012569256B2

(12) United States Patent
Srivastava

(10) Patent No.: US 12,569,256 B2
(45) Date of Patent: Mar. 10, 2026

(54) MULTI-FIRE CLIP APPLIER INSTRUMENT

(71) Applicant: SSI IP HOLDINGS INC., Fort Lauderdale, FL (US)

(72) Inventor: Sudhir Prem Srivastava, Haryana (IN)

(73) Assignee: SSI IP HOLDINGS INC., Fort Lauderdale, FL (US)

( * ) Notice: Subject to any disclaimer, the term of this patent is extended or adjusted under 35 U.S.C. 154(b) by 165 days.

(21) Appl. No.: 18/287,993

(22) PCT Filed: Nov. 4, 2022

(86) PCT No.: PCT/IN2022/050972
§ 371 (c)(1),
(2) Date: Oct. 23, 2023

(87) PCT Pub. No.: WO2023/079578
PCT Pub. Date: May 11, 2023

(65) Prior Publication Data
US 2024/0188963 A1     Jun. 13, 2024

(30) Foreign Application Priority Data
Nov. 5, 2021     (IN) .............................. 202111045154

(51) Int. Cl.
*A61B 17/128* (2006.01)
*A61B 34/37* (2016.01)

(52) U.S. Cl.
CPC .......... *A61B 17/1285* (2013.01); *A61B 34/37* (2016.02)

(58) Field of Classification Search
CPC ............................ A61B 17/1285; A61B 34/37
See application file for complete search history.

(56) References Cited

U.S. PATENT DOCUMENTS 6,277,131 B1 * 8/2001 Kalikow ............ A61B 17/1285
227/19
2019/0125347 A1 * 5/2019 Stokes ............... A61B 17/2909

FOREIGN PATENT DOCUMENTS

EP          3476334 A1     5/2019

* cited by examiner

*Primary Examiner* — Richard G Louis
(74) *Attorney, Agent, or Firm* — SZDC Law PC

(57) ABSTRACT

The present invention discloses a surgical instrument, such as a clip applier which can be configured to apply one or more clips to a vessel located within a surgical site in the patient. The clip applier can be structured and arranged to position a clip relative to the vessel in order to compress the vessel within the clip. The clip applier can be configured to deform the clip within the jaws. The end effector of the clip applier can include a replaceable clip cartridge.

5 Claims, 9 Drawing Sheets

305

409

401

403b

403a

405

407

MULTI-FIRE CLIP APPLIER INSTRUMENT

CROSS-REFERENCE TO RELATED APPLICATIONS AND PRIORITY

This application is the National Stage Application of International Application No. PCT/IN2022/050972, filed on Nov. 4, 2022, which application claims priority from Indian Patent Application No. 202111045154, filed on Nov. 5, 2021.

FIELD OF THE DISCLOSURE

The present invention generally relates to a robotic surgical system for minimally invasive surgery. More particularly, the invention relates to a clip applier with multiple clips stacked within a surgical instrument of the robotic surgical system.

BACKGROUND OF THE DISCLOSURE

This section is intended to introduce the reader to various aspects of art that may be related to various aspects of the present disclosure, which are described below. This disclosure is believed to be helpful in providing the reader with background information to facilitate a better understanding of the various aspects of the present disclosure. Accordingly, it should be understood that these statements are to be read in this light, and not just as admissions of prior art.

Robotically assisted surgical systems have been adopted worldwide to replace conventional surgical procedures to reduce amount of extraneous tissue(s) that may be damaged during surgical or diagnostic procedures, thereby reducing patient recovery time, patient discomfort, prolonged hospital tenure, and particularly deleterious side effects. In robotically assisted surgeries, the surgeon typically operates a master controller at a surgeon console to seamlessly capture and transfer complex actions performed by the surgeon giving the perception that the surgeon is directly articulating surgical tools to perform the surgery. The surgeon operating on the surgeon console may be located at a distance from a surgical site or may be located within an operating theatre where the patient is being operated.

The robotically assisted surgeries have revolutionized the medical field and one of the fastest growing sectors in medical device industry. However, the major challenge in robotically assisted surgeries is to ensure safety and precision during the surgery. One of the key areas of robotically assisted surgeries is the development of surgical robots for minimally invasive surgery. Over the last couple of decades, surgical robots have evolved exponentially and have been a major area of innovation in the medical device industry.

The robotically assisted surgical systems comprise of multiple robotic arms aiding in conducting robotic surgeries. The robotically assisted surgical system utilizes a sterile barrier to separate the non-sterile section of the robotic arm from a mandatory sterile surgical instrument attached to the robotic arm at an operating end. The sterile barrier may include a sterile plastic drape that envelops the robotic arm and a sterile adapter that operably engages with the sterile surgical instrument in a sterile field. The sterile barrier also may include a flexing drape interface to retain a drape section there between such that the torque and other force feedback is received as an input from both the sterile surgical instrument as well as the robotic arm. The sterile barrier is maintained between the sterile surgical instrument and the non-sterile robotic system. The sterile adapter detachably engages with an actuator assembly which drives and controls the sterile surgical instrument in a sterile field.

Various surgical instruments are used in robotic surgery for performing different surgical tasks. One such instrument is a clip applier which may be used to apply surgical clips to a vessel, duct, shunt, etc., during a surgical procedure. The clips in the clip applier instrument are generally loaded from a clip cartridge and then inserted within the patient body to clip the vessel. Further, there are other clip applier instrument in which the clips are stacked at the distil end of the clip applier instrument and thereby the clip applier instruments can be used for multiple clipping of vessels inside the patient body without the need to every time reload the clips in the jaws of the clip applier instrument.

In the light of aforementioned challenges, there is a need for an improved clip applier instrument in which the clips can be safely loaded.

BRIEF DESCRIPTION OF THE DRAWINGS

To further clarify advantages and features of the present disclosure, a more particular description of the disclosure will be rendered by reference to specific embodiments thereof, which is illustrated in the appended drawings. It is appreciated that these drawings depict only typical embodiments of the disclosure and are therefore not to be considered limiting of its scope. The disclosure will be described and explained with additional specificity and detail with the accompanying drawings in which.

DETAILED DESCRIPTION OF THE DISCLOSURE

Figure 1A:
FIG. 1(a) illustrates a schematic diagram of multiple robotic arms of a robotic surgical system in accordance with an embodiment of the disclosure.

For the purpose of promoting an understanding of the principles of the disclosure, reference will now be made to the embodiment illustrated in the drawings and specific language will be used to describe the same. It will nevertheless be understood that no limitation of the scope of the disclosure is thereby intended, such alterations and further modifications in the illustrated system, and such further applications of the principles of the disclosure as illustrated therein being contemplated as would normally occur to one skilled in the art to which the disclosure relates.

It will be understood by those skilled in the art that the foregoing general description and the following detailed description are exemplary and explanatory of the disclosure and are not intended to be restrictive thereof. Throughout the patent specification, a convention employed is that in the appended drawings, like numerals denote like components.

Reference throughout this specification to "an embodiment", "another embodiment", "an implementation", "another implementation" or similar language means that a particular feature, structure, or characteristic described in connection with the embodiment is included in at least one embodiment of the present disclosure. Thus, appearances of the phrase "in an embodiment", "in another embodiment", "in one implementation", "in another implementation", and similar language throughout this specification may, but do not necessarily, all refer to the same embodiment.

The terms "comprises", "comprising", or any other variations thereof, are intended to cover a non-exclusive inclusion, such that a process or method that comprises a list of steps does not include only those steps but may include other steps not expressly listed or inherent to such process or method. Similarly, one or more devices or sub-systems or elements or structures proceeded by "comprises . . . a" does not, without more constraints, preclude the existence of other devices or other sub-systems or other elements or other structures or additional devices or additional sub-systems or additional elements or additional structures.

Unless otherwise defined, all technical and scientific terms used herein have the same meaning as commonly understood by one of ordinary skill in the art to which this disclosure belongs. The apparatus, system, and examples provided herein are illustrative only and not intended to be limiting.

The terms "a" and "an" herein do not denote a limitation of quantity, but rather denote the presence of at least one of the referenced items. Further, the term sterile barrier and sterile adapter denotes the same meaning and may be used interchangeably throughout the description.

Embodiments of the disclosure will be described below in detail with reference to the accompanying drawings.

The disclosure relates to a robotic surgical system for minimally invasive surgery. The robotic surgical system will generally involve the use of multiple robotic arms. One or more of the robotic arms will often support a surgical tool which may be articulated (such as jaws, scissors, graspers, needle holders, micro dissectors, staple appliers, tackers, suction/irrigation tools, clip appliers, or the like) or non-articulated (such as cutting blades, cautery probes, irrigators, catheters, suction orifices, or the like). One or more of the robotic arms will often be used to support one or more surgical image capture devices such as an endoscope (which may be any of the variety of structures such as a laparoscope, an arthroscope, a hysteroscope, or the like), or optionally, some other imaging modality (such as ultrasound, fluoroscopy, magnetic resonance imaging, or the like).

The present disclosure is directed to robotic surgical systems, devices, methods, and computer-readable media that mitigate safety risks stemming from surgeon distraction from engagement with robotic surgical systems during surgical robotic procedures. More particularly, the present disclosure relates to systems and methods for identifying disengagement of a user using the robotic surgical system and causing the robotic surgical system to operate in one or more safe modes when the user is disengaged, thereby mitigating the risk that the user unintentionally injures the patient or otherwise compromises the surgical procedure by actuating the robotic surgical system while distracted. The systems and methods described herein provide various techniques for tracking a user position relative to a display of a surgeon console and, based on the tracked user position, determining whether the user is disengaged from a surgeon console, even for open-console architectures. If the user is disengaged from the surgeon console, the robotic surgical system is operated in one or more safe modes. Utilizing the technologies, techniques, and embodiments described herein, users are provided with a safer operating environment in which to perform robotic surgeries, and patients are afforded a safer environment in which to receive surgical treatment via robotic surgical systems.

Embodiments of the present disclosure are now described in detail with reference to the drawings in which like reference numerals designate identical or corresponding elements in each of the several views. As used herein, the terms "user" and "clinician" refer to a doctor, a surgeon, a nurse, technician, medical assistant, or similar support personnel or any other person that may use the robotic surgical systems described herein. Additionally, in the drawings and in the description that follows, terms such as front, rear, upper, lower, top, bottom, and similar directional terms are used simply for convenience of description and are not intended to limit the disclosure. In the following description, well-known functions or constructions are not described in detail to avoid obscuring the present disclosure in unnecessary detail.

FIG. 1(a) illustrates a schematic diagram of multiple robotic arms of a robotic surgical system in accordance with an embodiment of the disclosure. Specifically, FIG. 1 illustrates the robotic surgical system (100) having four robotic arms (103a), (103b), (103c), (103d) mounted around a patient cart (101). The four-robotic arms (103a), (103b), (103c), (103d) as depicted in FIG. 1 is for illustration purpose and the number of robotics arms may vary depending upon the type of surgery or the robotic surgical system. The four robotic arms (103a), (103b), (103c), (103d) are mounted along the patient cart (101) and may be arranged in different manner but not limited to the robotic arms (103a), (103b), (103c), (103d) mounted on the patient cart (101) or the robotic arms (103a), (103b), (103c), (103d) separately mounted on a movable means or the robotic arms (103a), (103b), (103c), (103d) mechanically and/or operationally connected with each other or the robotic arms (103a), (103b), (103c), (103d) connected to a central body (105) such that the robotic arms (103a), (103b), (103c), (103d) branch out of the central body (105).

Figure 1B:
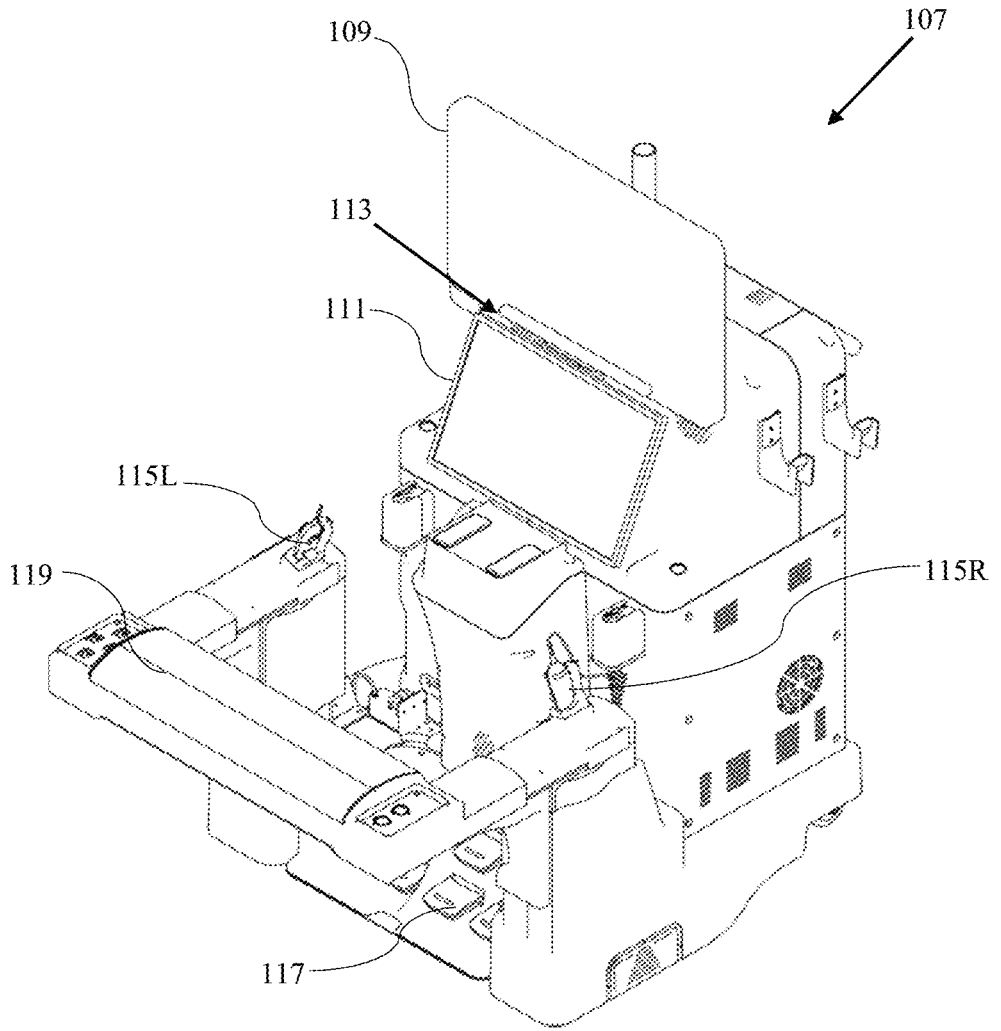
FIG. 1(b) illustrates a schematic diagram of a surgeon console of the robotic surgical system in accordance with an embodiment of the disclosure.

FIG. 1(b) illustrates a schematic diagram of a surgeon console of the robotic surgical system in accordance with an embodiment of the disclosure. The surgeon console (117) aids the surgeon to remotely operate the patient lying on the patient cart (101) by controlling the robotic arms (103a), (103b), (103c), (103d) inside the body of the patient. The surgeon console (117) is configured to control the movement of surgical instruments (as shown in FIG. 2(a)) while the instruments are inside the patient. The surgeon console (117) may comprise of at least an adjustable viewing means (107) but not limited to 2D/3D monitors, wearable viewing means (not shown) and in combination thereof. The surgeon console (117) may be equipped with multiple displays which would not only show 3D high definition (HD) endoscopic view of a surgical site at the patient cart (101) but may also shows additional information from various medical equipment's which surgeon may use during the robotic surgery. Further, the viewing means (107) may provide various modes of the robotic surgical system (100) but not limited to identification and number of robotic arms attached, current tool type attached, current tool tip position, collision information along with medical data like ECG, ultrasound display, fluoroscopic images, CT, MRI information. The surgeon console (117) may further comprise of mechanism for controlling the robotics arms but not limited to one or more hand controllers (109), one or more foot controllers (113), a clutch mechanism (not shown), and in combination thereof. The hand controllers (109) at the surgeon console (117) are required to seamlessly capture and transfer complex actions performed by surgeon giving the perception that the surgeon is directly articulating the surgical tools. The different controllers may be required for different purpose during the surgery. In some embodiments, the hand controllers (109) may be one or more manually operated input devices, such as a joystick, exoskeletal glove, a powered and gravity-compensated manipulator, or the like. These hand controllers (109) control teleoperated motors which, in turn, control the movement of the surgical instruments attached to the robotic arms. The surgeon may sit on a resting apparatus such as a chair (111), as depicted in FIG. 1(b), while controlling the surgeon console (117). The chair (111) may be adjustable with means in height, elbow rest and the like according to the ease of the surgeon and also various control means may be provided on the chair (111). Further, the surgeon console (117) may beat a single location inside an operation theatre or may be distributed at any other location in the hospital provided connectivity to the robotics arms is maintained.

Figure 1C:
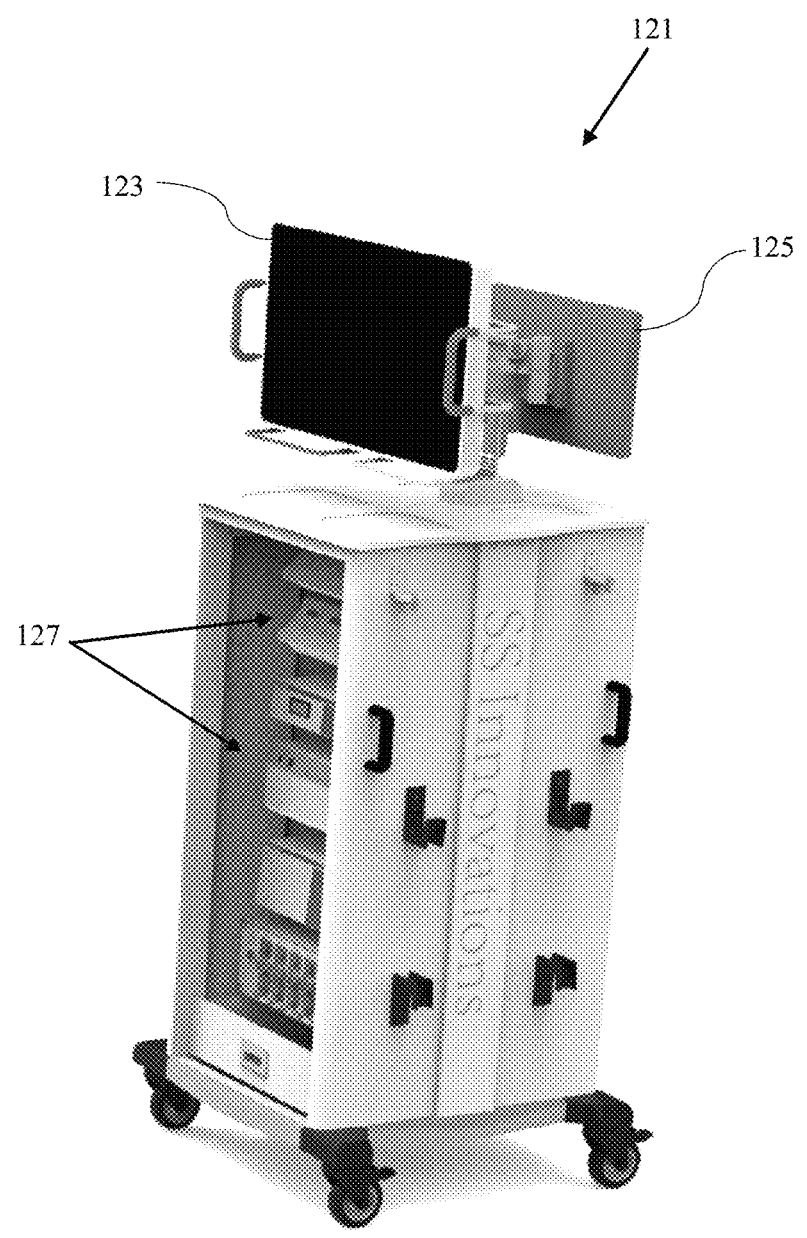
FIG. 1(c) illustrates a schematic diagram of a vision cart of the robotic surgical system in accordance with an embodiment of the disclosure.

FIG. 1(c) illustrates a schematic diagram of a vision cart of the robotic surgical system in accordance with an embodiment of the disclosure. The vision cart (119) is configured to display the 2D and/or 3D view of the operation captured by an endoscope. The vision cart (119) may be adjusted at various angles and heights depending upon the ease of view. The vison cart (119) may have various functionalities but not limited to providing touchscreen display, preview/recording/playback provisions, various inputs/outputs means, 2D to 3D converters and the like. The vision cart (119) may include a vision system portion (115a),(115b) such as TV screens, that enables a spectator or other non-operating surgeons to view a surgical site from outside the patient's body. One of the robotics arms typically engages a surgical instrument that has a video-image-capture function (i.e., a camera instrument) for displaying the captured images on the vision cart (119). In some robotic surgical system configurations, the camera instrument includes optics that transfer the images from the distal end of the camera instrument to one or more imaging sensors (e.g., CCD or CMOS sensors) outside of the patient's body. Alternatively, the imaging sensor(s) may be positioned at the distal end of the camera instrument, and the signals produced by the sensor(s) may be transmitted along a lead or wirelessly for processing and display on the vision cart (119).

Figure 2:
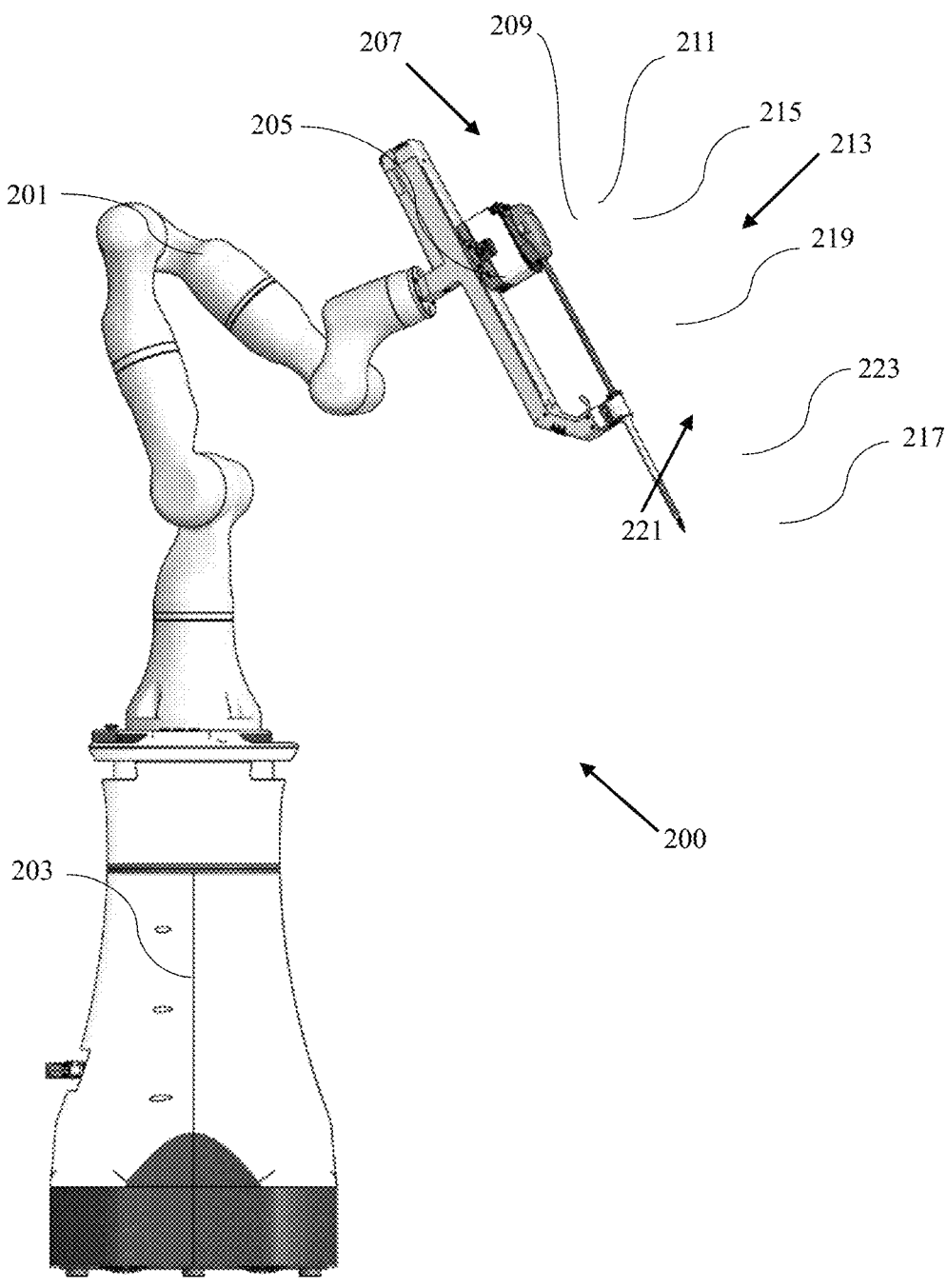
FIG. 2 illustrates a perspective view of a tool interface assembly mounted on a robotic arm in accordance with an embodiment of the disclosure.

FIG. 2 illustrates a perspective view of a tool interface assembly mounted on a robotic arm in accordance with an embodiment of the disclosure. The tool interface assembly (200) is mounted on the robotic arm (201) of the robotic surgical system (100). The tool interface assembly (200) is the main component for performing the robotic surgery on a patient. The robotic arm (201) as shown in FIG. 2 is shown for the illustration purpose only and other robotic arms with different configurations, degree of freedom (DOF) and shapes may be used.

The tool interface assembly (200), as depicted by FIG. 2, comprises of an ATI (Arm and Tool Interface) connector (203) which facilitates the tool interface (200) to operationally connect with the robotic arm. Further, the tool interface (200) further comprises of an actuator assembly (205) mounted on a guiding mechanism and capable of linearly moving along the guiding mechanism. The guiding mechanism depicted in FIG. 2 is a guide rail (207). The movement of the actuator assembly (205) along the guide rail (207) is controlled by the surgeon with the help of controllers on the surgeon console (117) as shown in FIG. 1(b). A sterile adapter assembly (209) is releasably mounted on the actuator assembly (205) to separate a non-sterile part of the robotic arm from a sterile surgical tool assembly (211). A locking mechanism (not shown) is provided to releasably lock and unlock the sterile adapter assembly (209) with the actuator assembly (205). The sterile adapter assembly (209) detachably engages from the actuator assembly (205) which drives and controls the sterile surgical instrument in a sterile field. In another embodiment, the surgical tool assembly (211) also may releasably lock/unlock or engages/disengages with the sterile adapter assembly (209) by means of a push button (213).

The surgical tool assembly (211) includes a shaft (215) and end effectors (217). The end effector (217) may comprise of a surgical instrument or may be configured to attach a surgical instrument. The surgical tool assembly (211) may also contain stored (e.g., on a semiconductor memory inside the instrument) information that may be permanent or may be updatable by the robotic surgical system (100).

A cannula gripper (219) is provided on the tool interface assembly (200) and is configured to grip a cannula (221) which receives the shaft (215) through an opening (not shown). The cannula (221) comprises of a hollow body which comprises of grooves (not shown) in an internal surface (not shown). The grooves provide a locking mechanism that fixes the cannula (221) to the shaft (215) at desired angle and precludes shifting, twisting or any axial movement of the shaft (215) once received by the cannula (221). The cannula gripper (219) is detachably attached to one end of the tool interface assembly (200) and comprises of flap like body which receives the cannula (221). Alternatively, the cannula gripper (219) may have a circular body for receiving the cannula (221) and comprise of grooves to grip the cannula (221) at a stationary position.

The cannula gripper (219) may be affixed to the body of the tool interface assembly (200) and may be configured to grip or secure the cannula (221) such that cannula (221) is stable while performing surgical operations. The cannula gripper (219) may be affixed to a mount (223) of the tool interface assembly (200) by way of receiving the cannula gripper (219) within a set of grooves of the mount (223).

Figure 3A:
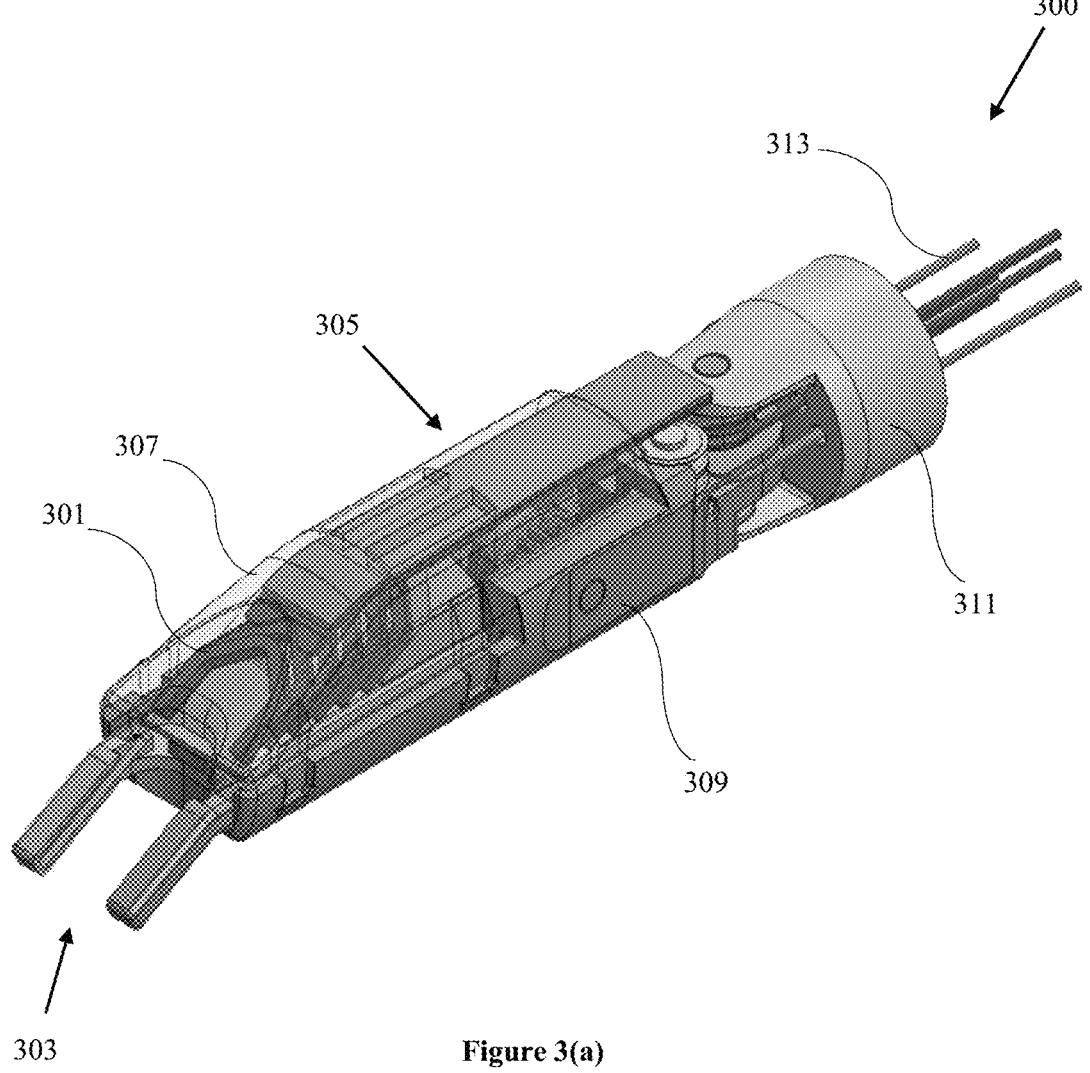
FIG. 3(a) illustrates a perspective view of an end effector of a clip applier in accordance with an embodiment of the disclosure.
Figure 3B:
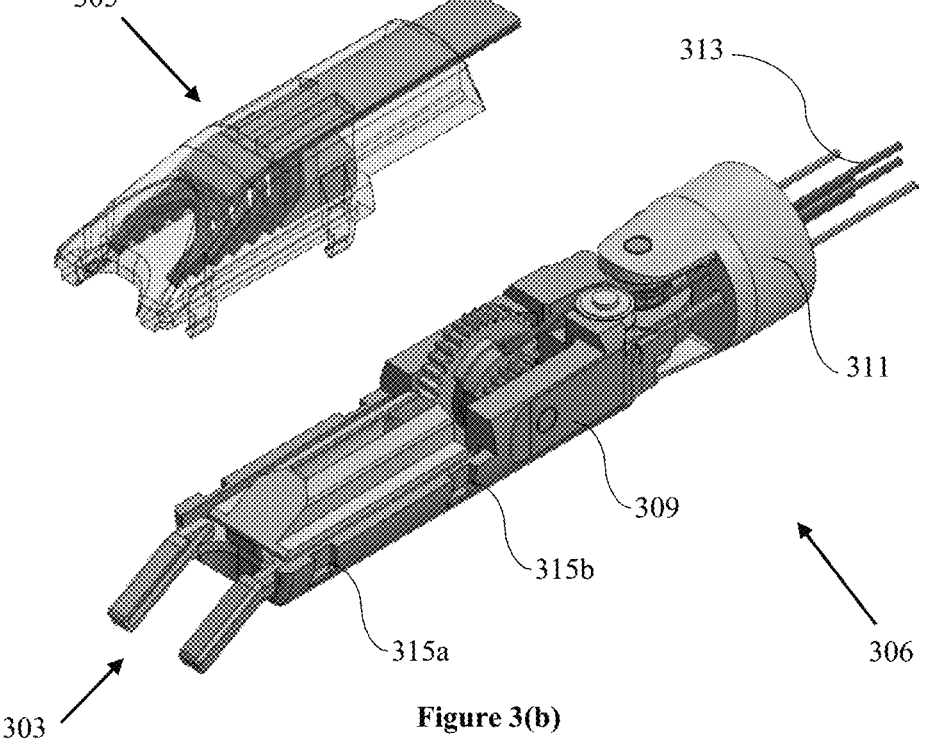
FIG. 3(b) illustrates a split view of a cartridge and the end effector of the clip applier in accordance with an embodiment of the disclosure.

FIG. 3(a) illustrates a perspective view of an end effector of a clip applier and FIG. 3(b) illustrates a split view of a cartridge and the end effector of the clip applier in accordance with an embodiment of the disclosure. A surgical instrument, such as a clip applier (300), can be configured to apply one or more clips to a vessel located within a surgical site in the patient. The clip applier (300) can be structured and arranged to position a clip (301) relative to the vessel in order to compress the vessel within the clip (301). The clip applier (300) can be configured to deform the clip (301) within the jaws (303). The end effector of the clip applier (300) can include a replaceable clip cartridge (305). The clip cartridge (305) can comprise a housing (307) and a plurality of clips (301) positioned within the housing (307). The housing (307) can comprise a storage chamber in which the clips (301) can be stacked. The storage chamber can comprise sidewalls which extend around, or at least substantially around, the perimeter of the clips (301). The stack of clips (301) depicted in FIG. 3-5 comprises six clips (301), for example; however, other embodiments are envisioned in which the stack of clips (301) can include more than six clips (301) or less than six clips (301). The clip cartridge (305) is mounted on a base (309) and the base (309) includes plurality of slots (315*a*, 315*b*). The proximal end of the end effector of the clip applier (300) consists of a clevis (311). A plurality of wires (313) straps through the clevis (311) to facilitate pitch movement of the end effector of the clip applier (300).

Figure 4A:
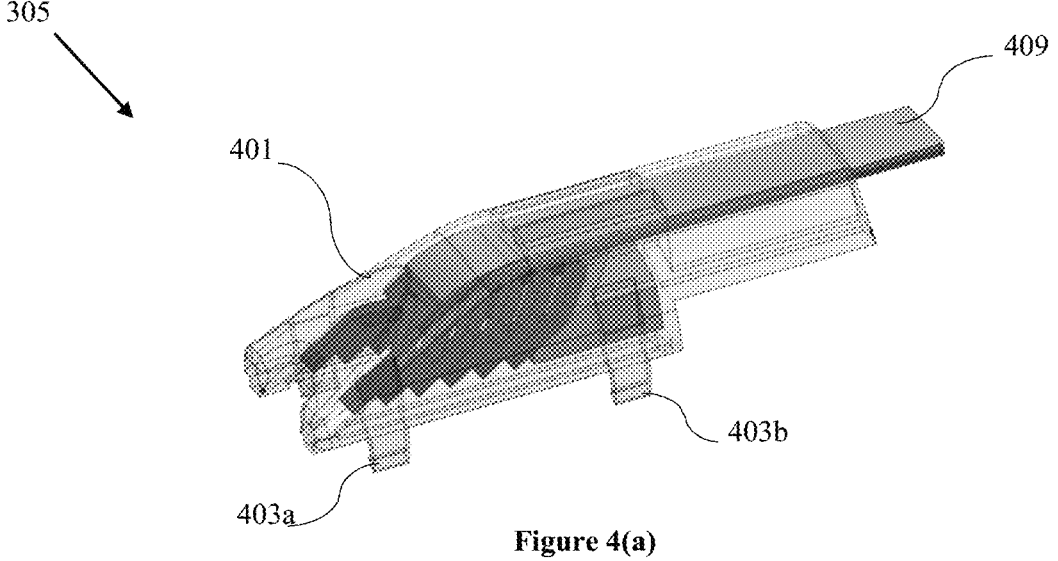
FIG. 4(a) illustrates the cartridge assembly of the clip applier in accordance with an embodiment of the disclosure.
Figure 4B:
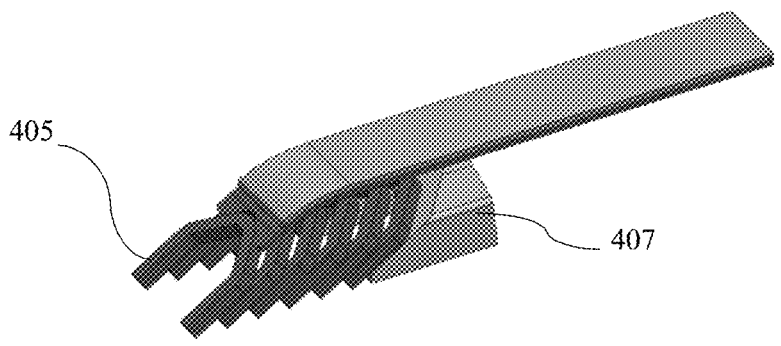
FIG. 4(b) illustrates a cartridge assembly of the clip applier without outer cover in accordance with an embodiment of the disclosure.

FIG. 4(*a*) illustrates a cartridge assembly of the clip applier; FIG. 4(*b*) illustrates the cartridge assembly of the clip applier without outer cover and FIG. 4(*c*) illustrates a bottom view of the cartridge assembly of the clip applier in accordance with an embodiment of the disclosure. The cartridge assembly (305) comprises a housing (401) in which plurality of clips (405) are stacked. The housing (401) includes plurality of protruding portion (403*a*, 403*b*) which fits into the slots (315*a*, 315*b*) of the base (309) (as illustrated in FIG. 3*b*) to lock the cartridge assembly (305) to the clip applier. The cartridge assembly (305) further comprises a pusher (407) against which all the clips (405) are stacked. A feeder bar (409) can be positioned with the housing (401) such that it is always configured in a firing position against the first clip (405) stacked within the housing (401). The pusher (407) may be configured in such a manner that it advances the clips (405) upon firing of the first clip (405). The pusher (407) at the bottom side includes a hook shape portion (407*a*) along which a biasing member is mounted which can facilitate in advancing the clips (405) forwardly. Further, at the proximal end of the bottom side of the feeder bar (409) includes a tooth like shape (411) to facilitate the movement of the feeder bar (409) forwardly and backwardly.

Figure 4C:
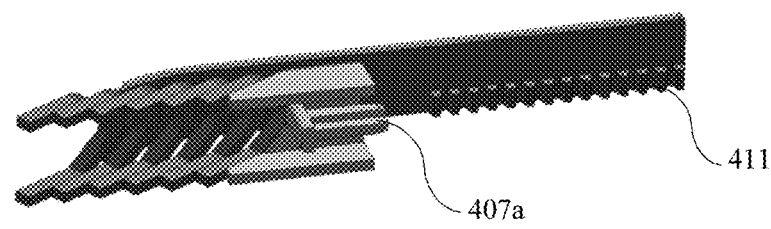
FIG. 4(c) illustrates a bottom view of the cartridge assembly of the clip applier in accordance with an embodiment of the disclosure.
Figure 5A:
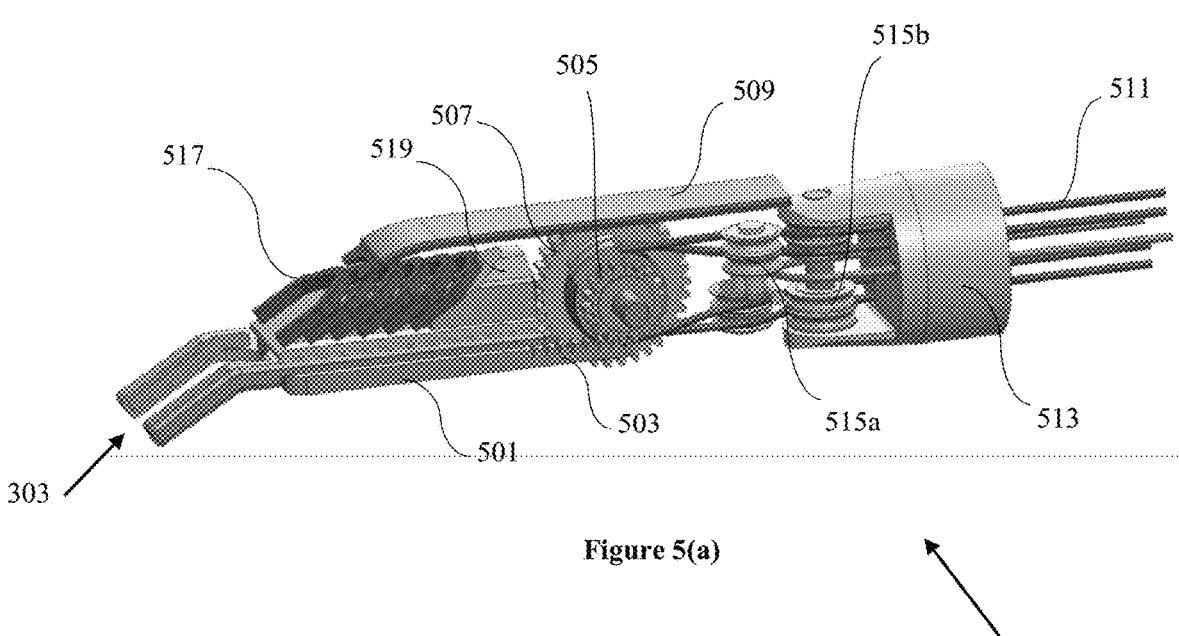
FIG. 5(a) illustrates a perspective view of the end effector of the clip applier without the outer cover in accordance with an embodiment of the disclosure.
Figure 5B:
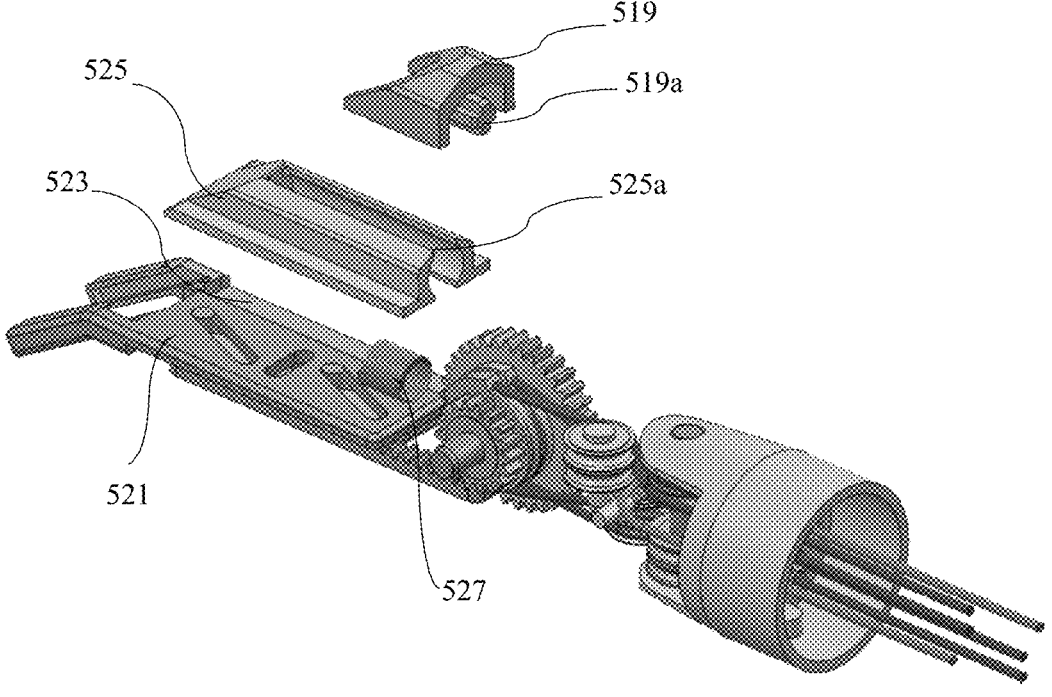
FIG. 5(b) illustrates a split view of a clip feeding mechanism of the end effector of the clip applier in accordance with an embodiment of the disclosure.

FIG. 5(*a*) illustrates a perspective view of an end effector of a clip applier without the outer cover; and FIG. 5(*b*) illustrates split view of clip feeding mechanism of the end effector of a clip applier in accordance with an embodiment of the disclosure. FIG. 5(*a*) and FIG. 5(*b*) may collectively be represented as drive assembly (306). The end-effector of the clip applier comprises a jaw actuator (501) which is configured to closing and opening of the jaws (303). The jaw actuator (501) at its proximal end includes a tooth like profile (503) which engages with jaw actuation gear (505). A feeder wheel gear (507) placed adjacent to the jaw actuation gear (507). The feeder wheel gear (507) is engaged with the proximal end of a feeder bar (509). The proximal end of the feeder bar (509) includes a tooth like profile (as illustrated in FIG. 4*c*). Further, a set of wires (511) through the clevis (513) straps around the pulleys (515*a*, 515*b*) to facilitate the jaw actuation and feeding of the clips (517) in the jaws (303). As illustrated in FIG. 5(*b*), a left jaw (521) and a right jaw (523) are placed on the jaw actuator (501). A clip rail (525) sits over the jaws (521, 523). The clip rail (525) includes an opening (525*a*) along its top surface to encompass the pusher (519). The pusher (519) is configured to move forwardly along the opening (525*a*) of the clip rail (525). Further, the pusher (519) at its proximal end has a protruding profile (519*a*) along with a compression spring (527).

The foregoing descriptions of exemplary embodiments of the present disclosure have been presented for purposes of illustration and description. They are not intended to be exhaustive or to limit the disclosure to the precise forms disclosed, and obviously many modifications and variations are possible in light of the above teaching. The exemplary embodiment was chosen and described in order to best explain the principles of the disclosure and its practical application, to thereby enable others skilled in the art to best utilize the disclosure and various embodiments with various modifications as are suited to the particular use contemplated. It is understood that various omissions, substitutions of equivalents are contemplated as circumstance may suggest or render expedient but is intended to cover the application or implementation without departing from the spirit or scope of the claims of the present disclosure.

Benefits, other advantages, and solutions to problems have been described above with regard to specific embodiments. However, the benefits, advantages, solutions to problems, and any component(s) that may cause any benefit, advantage, or solution to occur or become more pronounced are not to be construed as a critical, required, or essential feature or component of any or all the claims.

While specific language has been used to describe the disclosure, any limitations arising on account of the same are not intended. As would be apparent to a person in the art, various working modifications may be made to the apparatus in order to implement the inventive concept as taught herein.

I claim:

1. A multi fire clip applier surgical instrument (300) comprising:
   a replaceable clip cartridge assembly (305), the replaceable clip cartridge assembly (305) including a housing (307, 401) with at least a protruding portion (403);
   a base (309), wherein the base (309) includes at least a slot (315) in which the protruding portion (403) of the housing (307) is secured; and
   a drive assembly (306) for actuating the multi fire clip applier surgical instrument (300), wherein the driveassembly (306) comprising:
       a plurality of jaws assembly (303) including a left jaw (521) and a right jaw (523);
       a jaw actuator (501), wherein the jaw actuator (501) at its proximal end includes a tooth like profile (503);
       a jaw actuation gear (505);
       a feeder wheel gear (507);
       a clip rail (525); and
       a compression spring (527);
   wherein the jaw actuation gear (505) is configured to engage with the tooth like shape (503) of the proximal end of the jaw actuator (501) to facilitate the opening and closing of the left jaw (521) and the right jaw (523).

2. The multi fire clip applier surgical instrument (300) as claimed in claim 1, wherein the replaceable clip cartridge assembly (305) comprises a plurality of clips (301, 405, 517), a pusher (407, 519), and a feeder bar (409, 509).

3. The multi fire clip applier surgical instrument (300) as claimed in claim 2, wherein the feeder bar (409, 509) includes a tooth like shape (411) at its proximal end to facilitate movement of the feeder bar (409, 509) in forward and backward direction.

4. The multi fire clip applier surgical instrument (300) as claimed in claim 2, wherein the pusher (407, 519) includes a hook shape portion (407*a*) to facilitate in advancing the plurality of clips (301, 405, 517).

5. The multi fire clip applier surgical instrument (300) as claimed in claim 1, wherein the feeder wheel gear (507) is configured to engage with the tooth like shape (411) of the proximal end of the feeder bar (409, 509) to facilitate movement of the feeder bar (409, 509) in forward and backward direction.

\* \* \* \* \*